United States Patent
Yamaguchi (10) Patent No.: US 7,956,320 B2
(45) Date of Patent: Jun. 7, 2011

(54) DATA PROCESSOR FOR MASS SPECTROMETER

(75) Inventor: Shinichi Yamaguchi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 242 days.

(21) Appl. No.: 12/301,306

(22) PCT Filed: May 18, 2006

(86) PCT No.: PCT/JP2006/309947
§ 371 (c)(1), (2), (4) Date: Nov. 18, 2008

(87) PCT Pub. No.: WO2007/135708
PCT Pub. Date: Nov. 29, 2007

(65) Prior Publication Data
US 2009/0230298 A1    Sep. 17, 2009

(51) Int. Cl.
*H01J 49/26* (2006.01)
(52) U.S. Cl. .......................... 250/281; 702/19
(58) Field of Classification Search .................. 250/281, 250/282; 702/19, 22, 23
See application file for complete search history.

(56) References Cited

U.S. PATENT DOCUMENTS 7,473,892 B2 * 1/2009 Sano et al. .................. 250/281
7,645,984 B2 * 1/2010 Gorenstein et al. .......... 250/281

FOREIGN PATENT DOCUMENTS

| JP | 61-020856 A | 1/1986 |
|---|---|---|
| JP | 64-009359 A | 1/1989 |
| JP | 03-089441 A | 4/1991 |
| JP | 10-142196 A | 5/1998 |
| JP | 10-293120 A | 11/1998 |
| JP | 2001-249114 A | 9/2001 |

OTHER PUBLICATIONS

Japanese Office Action for corresponding Patent Application No. 2008-516511; mailed Sep. 14, 2010 (with translation).

* cited by examiner

*Primary Examiner* — Kiet T Nguyen
(74) *Attorney, Agent, or Firm* — Sughrue Mion, PLLC

(57) ABSTRACT

A main peak list is created with the data obtained by an $MS^n$ analysis (S1), the difference between the mass-to-charge ratio of each product ion listed on this main peak list and that of the precursor ion is calculated (S2), and an auxiliary peak list for forming a virtual peak corresponding to the mass-to-charge ratio difference is created (S3). On the same graph, an $MS^n$ spectrum data is created so that each peak listed on the main peak list and each peak listed on the auxiliary peak list are drawn with different display colors (S4), and the $MS^n$ spectrum is displayed on the display screen (S5). Consequently, an $MS^n$ analysis result for a plurality of precursor ions with different mass-to-charge ratios becomes easy to be compared. In particular, it is possible to easily and visually determine whether or not a fragment having the same mass-to-charge ratio desorbed by a dissociation exists.

6 Claims, 5 Drawing Sheets

DATA PROCESSOR FOR MASS SPECTROMETER

TECHNICAL FIELD

The present invention relates to a data processor for a mass spectrometer, and more specifically to a data processor for processing the data obtained by a mass spectrometer which performs an $MS^n$ analysis.

BACKGROUND ART

In the field of mass analysis using an ion trap mass spectrometer or other apparatuses, a technique called the MS/MS analysis (or tandem analysis) is conventionally known. In a general MS/MS analysis, an ion having a specific mass number (mass-to-charge ratio m/z) is first selected as a precursor ion from an object to be analyzed. Next, the precursor ion thus selected is dissociated by a collision induced dissociation (CID) process to produce product ions. After that, the product ions are mass analyzed to obtain the information on the mass-to-charge ratio of the product ions and desorbed ions, and based on this information, the composition and chemical structure of the target sample molecule are deduced.

In recent years, samples having larger molecular weight than before have been analyzed with such an apparatus, and their chemical structures (composition) have also tended to become more complicated. Hence, depending on the quality of the sample, ions are often not dissociated to have a sufficiently small mass by only a one-stage dissociation operation. In such cases, an $MS^n$ analysis may be performed in which a dissociation operation is repeated multiple times and the product ions finally generated are mass analyzed (refer to Patent Documents 1 and 2 for example). The aforementioned MS/MS analysis is an $MS^n$ analysis in the case where n=2.

Generally, in mass spectrometers, a mass spectrum ($MS^n$ spectrum) in which a mass-to-charge ratio is assigned to the horizontal axis and a signal intensity (or relative intensity) to the vertical axis is created as a result of a mass analysis, and the mass spectrum is displayed on a display screen as one of the analysis results. In mass spectrometers capable of an $MS^n$ analysis, if a plurality of precursor ions having different mass-to-charge ratios are set as candidates to be selected, each $MS^n$ spectrum for every precursor ion is obtained.

Figure 9:
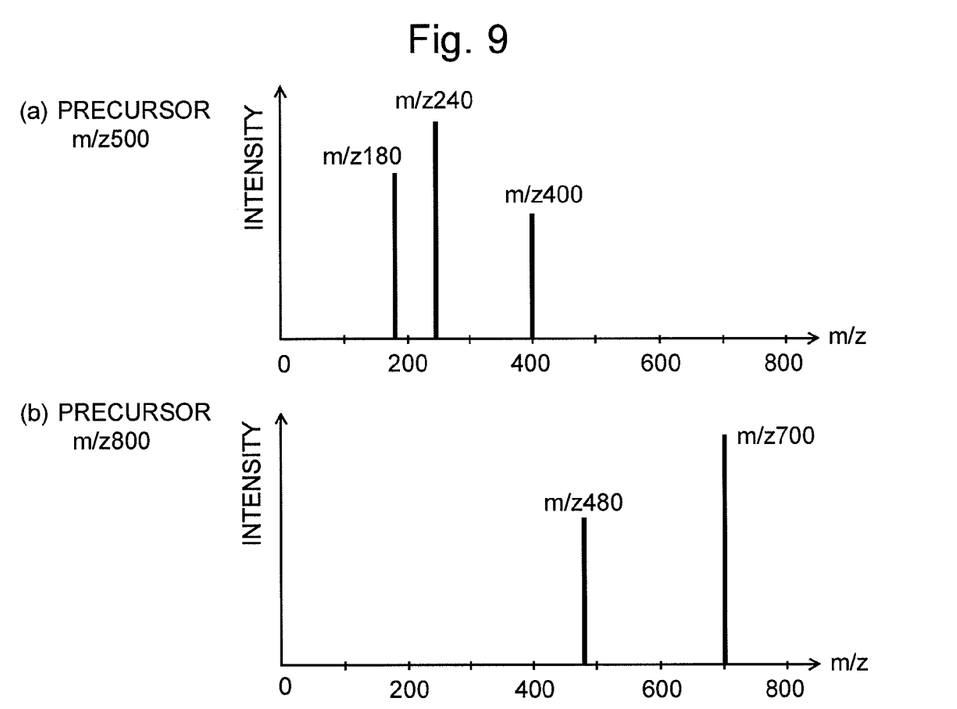
FIG. 9 is a diagram illustrating an example of the display of an MS$^n$ spectrum in a conventional mass spectrometer.

At this point, as an example, assume that the ions of m/z500 and m/z800 were selected as a precursor ion and an MS/MS analysis was performed for each of them, with the result that MS/MS spectra as illustrated in FIG. 9 were obtained. The position of each peak appearing on these MS/MS spectra indicates the mass-to-charge ratio of the product ions generated by the dissociation process. According to FIG. 9(a), it is understood that three kinds of product ions of m/z180, 240, and 400 are obtained in the case where m/z500 is set to be a precursor ion. According to FIG. 9(b), it is understood that two kinds of product ions of m/z480 and 700 are obtained in the case where m/z800 is set to be a precursor ion. In the cases for these examples, since almost all the precursor ions are dissociated by a dissociation operation, the peak corresponding to the precursor ion does not appear in the MS/MS spectra.

In an $MS^n$ analysis, when the precursor ion's chemical structure and composition are deduced and then the original sample molecule's structure and composition are deduced, the information about the mass-to-charge ratio of each product ion is important. Simultaneously, the mass information of the fragments removed in the process in which each product ion is generated is also important. However, even if a person in charge of an analysis looks at an $MS^n$ spectrum displayed as previously described in conventional apparatuses, it is not easy to intuitively obtain the information about the mass of the fragments removed in such a dissociation process.

In particular, in the case where the peak corresponding to a precursor ion clearly appears on an $MS^n$ spectrum, it is easy to mentally calculate the difference between the mass-to-charge ratio of the precursor ion and that of each product ion, i.e. the information of the mass of the removed fragments. However, in the case where the peak originating from the precursor ion can be hardly seen as in the example illustrated in FIG. 9, it is difficult to mentally perform the calculation as just described. In addition, in an $MS^n$ analysis, another important piece of information is whether or not there are desorbed fragments having the same mass for the dissociations of a plurality of precursor ions whose mass-to-charge ratios are different. However, it is also difficult to intuitively determine such a fact with an $MS^n$ spectrum displayed in conventional apparatuses as described earlier. Such inconveniences contribute to decreasing the working efficiency of the structure deduction based on the result of an $MS^n$ analysis.

[Patent document 1] Japanese Unexamined Patent Application Publication No. H10-142196
[Patent document 2] Japanese Unexamined Patent Application Publication No.

DISCLOSURE OF THE INVENTION

Problem to be Solved by the Invention

The present invention is accomplished to solve the aforementioned problem, and the main objective thereof is to provide a data processor for a mass spectrometer capable of providing, when a person in charge of an analysis performs an analytical process such as a chemical structure deduction by using a plurality of $MS^n$ spectra, easy-to-understand and pertinent information.

Means for Solving the Problem

A first aspect of the present invention developed to solve the aforementioned problem provides a data processor for a mass spectrometer, for processing data obtained by a mass spectrometer capable of performing an $MS^n$ analysis in which an ion having a specific mass-to-charge ratio is selected as a precursor ion from among ions obtained by an MS (where n is an integer equal to or more than two) analysis and an $MS^n$ analysis of an ion generated by a dissociation operation for the precursor ion is performed, including:

a) an $MS^n$ spectrum creator for creating spectrum data for displaying an $MS^n$ spectrum based on data obtained by an $MS^n$ analysis;

b) a mass-to-charge ratio difference calculator for calculating each difference between a mass-to-charge ratio of all or a portion of peaks appearing on the $MS^n$ spectrum and a mass-to-charge ratio of a precursor ion of the $MS^n$ analysis and/or a precursor ion of an $MS^2$ analysis through $MS^{n-1}$ analysis (where n is equal to or more than three in this case) which have been the basis of a creation of the $MS^n$ analysis' precursor ion;

c) an $MS^n$ mass-to-charge ratio difference spectrum creator for creating mass-to-charge ratio difference spectrum data for displaying an $MS^n$ mass-to-charge ratio difference spectrum having a peak at a position of each mass-to-charge ratio difference obtained by the mass-to-charge ratio difference calculator; and d) a spectrum merge section for creating a spectrum in which the MS$^n$ mass-to-charge ratio difference spectrum and the MS$^n$ spectrum are overlapped or combined in a manner that each peak appearing on both spectra can be visually discriminable, and the data processor for a mass spectrometer displaying the spectrum created by the spectrum merge section on a display screen.

In the spectrum merge section, in the case where the MS$^n$ spectrum and the MS$^n$ mass-to-charge ratio difference spectrum are completely overlapped, i.e. if the mass-to-charge ratio axis and the intensity axis are common to these spectra, both spectra's peaks are mixed. Then, in such a case, "visually discriminable" may be accomplished by the following manner: using different formats for the peak's line appearing on both spectra, such as a color, thickness, and type; and using different formats (such as a color) for a mass label for numerically displaying each peak's mass-to-charge ratio information.

In the case where the MS$^n$ spectrum and the MS$^n$ mass-to-charge ratio difference spectrum are combined in the spectrum merge section, at least either one of the mass-to-charge ratio axis and the intensity axis may be separated. Hence, the display area can be divided so that the both spectra's peaks are not mixed. This accomplishes the "visually discriminable" state.

A second aspect of the present invention developed to solve the aforementioned problem provides a data processor for a mass spectrometer, for processing data obtained by a mass spectrometer capable of performing an MS$^n$ analysis in which an ion having a specific mass-to-charge ratio is selected as a precursor ion from among ions obtained by an MS$^{n-1}$ (where n is an integer equal to or more than two) analysis and an MS$^n$ analysis of an ion generated by a dissociation operation for the precursor ion is performed, including:

a) an MS$^n$ spectrum creator for creating spectrum data for displaying an MS$^n$ spectrum based on data obtained by an MS$^n$ analysis; and b) an MS$^n$ spectrum modifier for, in a case where two precursor ions whose mass-to-charge ratio is different from each other are set to respectively perform an MS$^n$ analysis, calculating a mass-to-charge ratio difference between the two precursor ions and adding spectrum data so that a virtual peak in which a position of all or a portion of peaks appearing on the MS$^n$ spectrum is shifted by the mass-to-charge ratio difference is displayed on the MS$^n$ spectrum, and the data processor for a mass spectrometer displaying a spectrum based on the spectrum data added by the MS$^n$ spectrum modifier on a display screen.

EFFECTS OF THE INVENTION

In the data processor for a mass spectrometer according to the first aspect of the present invention, not only is an MS$^n$ spectrum in which a peak originating from the product ion by an MS$^n$ analysis displayed on the display screen, but an MS$^n$ mass-to-charge ratio difference spectrum in which a virtual peak appears in the position of the mass-to-charge ratio difference between each product ion and precursor ion is also displayed on the display screen. Therefore, a person in charge of the analysis can visually and intuitively obtain the mass information of the fragments desorbed and removed from the precursor ion in the dissociation operation in the MS$^n$ analysis, or the summation information of the masses of the fragments desorbed and removed from the original precursor ion by the multiple-stage dissociation operations. Consequently, in the case where two MS$^n$ analyses with a precursor ion whose mass-to-charge ratio is different from each other are performed to compare the results, it is possible to easily and visually know whether or not a fragment having the same mass exists in these MS$^n$ analyses, which leads to an efficient evaluation of an MS$^n$ analysis result. Furthermore, this contributes to the efficiency improvement of the analytic operation for the chemical structure of the substance to be targeted.

In the data processor for a mass spectrometer according to the second aspect of the present invention, on an MS$^n$ spectrum, which is the result of an MS$^n$ analysis of the first precursor ion and which is displayed on the display screen, not only does a peak originating from product ions by the MS$^n$ analysis appear, but a virtual peak also appears whose position is shifted on the mass-to-charge ratio axis by the mass-to-charge ratio difference between the first and second precursor ions. The position's shift on the mass-to-charge ratio axis by the mass-to-charge ratio difference corresponds to the corrective operation of the mass-to-charge ratio difference between both precursor ions in order to compare the mass of the fragments desorbed in the dissociation process in both MS$^n$ analyses. Hence, by visually judging whether or not the position of the virtual peak and that of the peak appearing on an MS$^n$ spectrum which is a result of an MS$^n$ analysis of the second precursor ion are the same, as in the case of the first aspect of the present invention, it is possible to easily know whether or not fragments having the same mass are existent in both analyses.

BEST MODES FOR CARRYING OUT THE INVENTION

Figure 1:
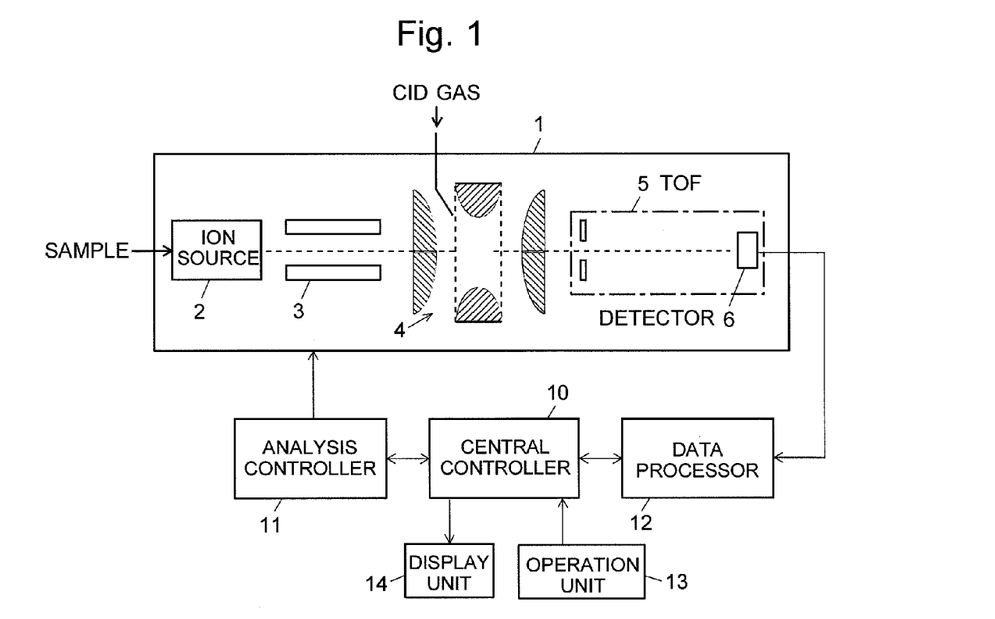
FIG. 1 is an overall configuration diagram of an embodiment of the mass analytical system having a data processor according to the present invention.

First, an embodiment of a mass analytical system having a data processor according to the first aspect of the present invention will be explained with reference to the figures. FIG. 1 is an overall configuration diagram of this mass analytical system.

A mass analyzer 1 includes: an ion source 2 for ionizing a sample molecule; an ion trap 4 for temporarily storing the ion in the internal space and for promoting the ion's CID in the internal space; an ion optical system 3 for guiding the ions generated in the ion source 2 to the ion trap 4; a time-of-flight mass separator (TOF) 5 for separating the ions released from the ion trap 4 according to the mass-to-charge ratio; and a detector 6 for detecting the ions separated by the TOF 5.

An analysis controller 11 performs, based on the indication from the central controller 10, an $MS^n$ analysis by controlling the operation of each unit of the mass analyzer 1. A data processor 12 receives the detection data obtained by the detector 6 and performs a predetermined data processing including a display processing which will be described later. To the central controller 10, an operation unit 13 and a display unit 14 are connected as a user interface. Most of the functions of the central controller 10, analysis controller 11, and data processor 12 can be realized by a personal computer including predetermined control/process software.

The basic operation of the mass analytical system with the aforementioned configuration will be roughly explained. In the case where a normal MS analysis is performed, the ion source 2 ionizes a sample molecule under the control of the analysis controller 11, and the various kinds of ions generated are introduced into the ion trap 4 through the ion optical system 3. In the ion trap 4, the ions are temporarily captured by the electric field formed by the voltage applied to the three-dimensional quadrupole electrodes. The ions captured are collectively launched at a predetermined timing to be introduced into the TOF 5. While flying in the flight space of the TOF 5, the time lag occurs for each ion according to the mass-to-charge ratio and each ion reaches in sequence the detector 6 to be detected.

The data processor 12 which has received the detection data converts the flight time in the TOF 5 into the mass-to-charge ratio to create a mass spectrum, and makes the mass spectrum displayed on the screen of the display unit 14 through the central controller 10. Based on this MS analysis result, the person in charge of the analysis determines the precursor ion as a target in the $MS^2$ analysis.

When the person in charge enters the mass-to-charge ratio of the precursor ion into the operation unit 13 and indicates the performance of the $MS^2$ analysis, the ion source 2 ionizes the sample molecule under the control of the analysis controller 11, and the various kinds of ions generated are introduced into the ion trap 4 through the ion optical system 3. In the ion trap 4, the ions are temporarily captured by the electric field as described earlier, and after that, the voltage which causes the undesired ions other than the set precursor ion to disperse is applied to each electrode and only the precursor ion is left in the capture space; i.e. the precursor ion's selection is performed. Then, a CID gas is directed into the capture space from the outside so as to help the precursor ion to be dissociated by colliding with the CID gas.

The product ions generated by the dissociation (and also the precursor ion if it remains) are launched collectively at a predetermined timing, and introduced into the TOF 5. While flying in the flight space of the TOF 5, the time lag occurs for each ion according to the mass-to-charge ratio and each ion reaches in sequence the detector 6 to be detected. The data processor 12 which has received the detection data converts the flight time in the TOF 5 into the mass-to-charge ratio to create an $MS^2$ spectrum, and makes the $MS^2$ spectrum displayed on the screen of the display unit 14 through the central controller 10. In order to perform an $MS^n$ analysis with n equal to or more than three, the following operation is repeated a plurality of times: one of the product ions generated by the CID in the ion trap 4 is selected as a precursor ion once again, and the precursor ion is dissociated by the CID.

Figure 2:
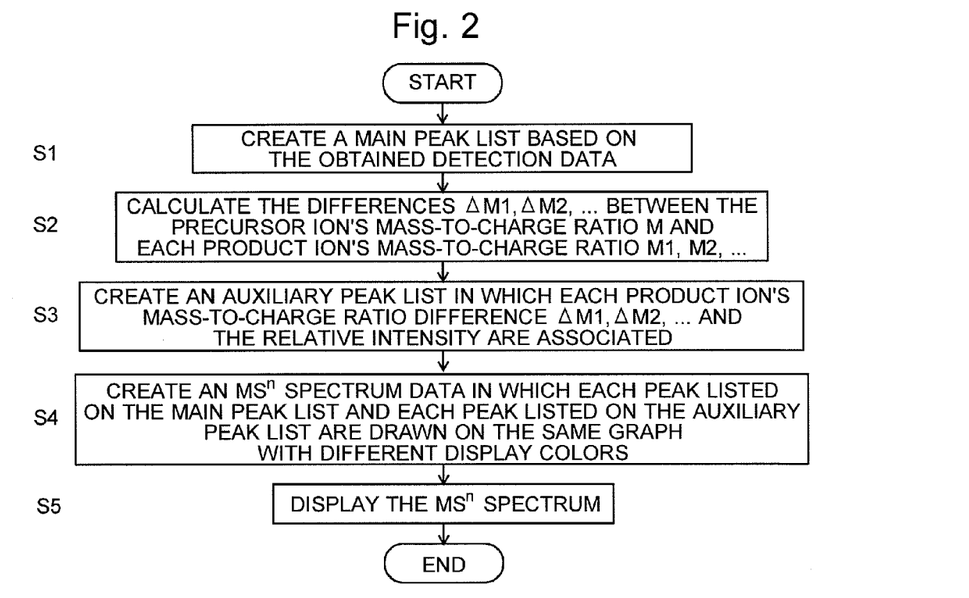
FIG. 2 is a flowchart illustrating the operation of an MS$^n$ spectrum display processing in the mass analytical system according to the present embodiment.

In the data processor 12 in the mass analytical system according to the present embodiment, a characteristic operation is performed when the data processor 12 receives the detection data by an $MS^n$ analysis as previously described to create an $MS^n$ spectrum to be displayed on the display unit 14. This operation will be explained with reference to FIGS. 2 and 3.

First, at the beginning of the operation, the flight time is converted to the mass-to-charge ratio based on the collected detection data and a main peak list is created in which a mass-to-charge ratio and the relative intensity according to the ion current's magnitude are associated (Step S1). If the peaks listed on the main peak list are illustrated on a graph in which a mass-to-charge ratio is assigned to the horizontal axis and a relative intensity to the vertical axis, a conventionally general $MS^n$ spectrum as illustrated in FIG. 9 is obtained.

Next, the differences $\Delta M1, \Delta M2, \ldots$ between the mass-to-charge ratios $M1, M2, \ldots$ of each product ion appearing on the $MS^n$ spectrum (i.e. listed on the main peak list) and the precursor ion's mass-to-charge ratio M are calculated (Step S2). Then, an auxiliary peak list is created which associates the mass-to-charge ratio differences $\Delta M1, \Delta M2, \ldots$ with the relative intensity of the product ions which the mass-to-charge ratio differences are obtained with (Step S3). In the example of FIG. 9(a) for instance, since the precursor ion's mass-to-charge ratio M is 500, the mass-to-charge ratio differences $\Delta M1, \Delta M2$, and $\Delta M3$ each corresponding to the product ions having mass-to-charge ratios M1=180, M2=240, and M3=400 are 320, 260 and 100, respectively. The auxiliary peak list includes these values and each peak's relative intensity associated with these values.

Figure 3:
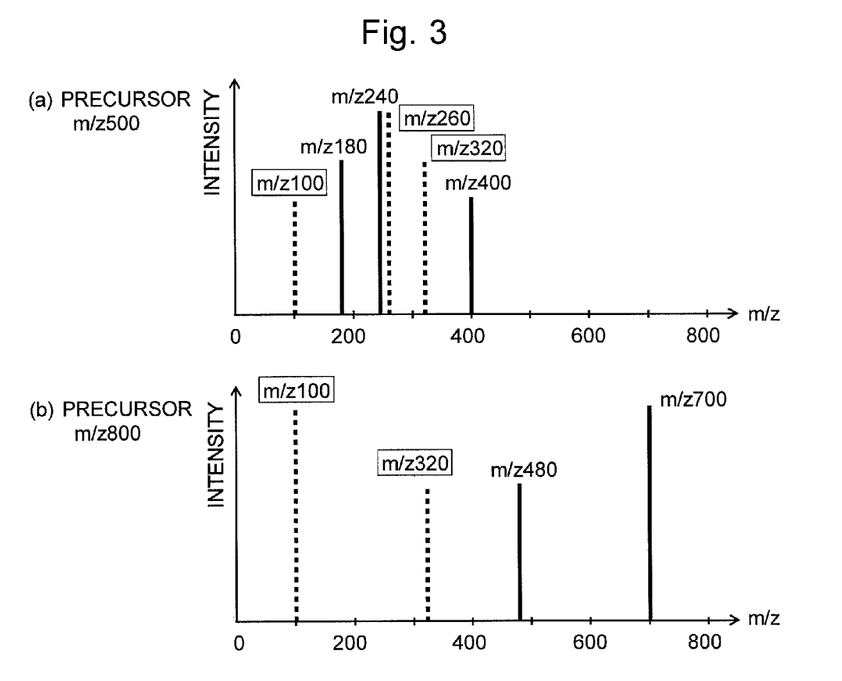
FIG. 3 is a diagram illustrating an example of the display of an MS$^n$ spectrum in the mass analytical system according to the present embodiment.

In the next step, an $MS^n$ spectrum data is created so that, on the same graph, i.e. on the graph having a common mass-to-charge ratio axis and intensity axis, each peak listed on the main peak list is drawn with a line having a predetermined display color (e.g. black) and each peak listed on the auxiliary peak list is drawn with a line having another display color (e.g. red) (Step S4). Then the $MS^n$ spectrum data is sent to the central controller 10 to be displayed on the screen of the display unit 14, and consequently an $MS^n$ spectrum as illustrated in FIG. 3(a) is drawn (Step S5). In FIG. 3, two different kinds of display colors are expressed with a solid line and dashed line respectively.

In FIG. 3(a), three peaks (which are illustrated with a solid line) originating from the product ion and three peaks (which are illustrated with a dashed line) virtually formed at a position of each mass-to-charge ratio difference are mixed. However, in order to individually associate the former with the latter, some display processing may be preferably performed, such as: the display color of a mass label which numerically indicates the mass-to-charge ratio m/z is set to be the same between the former and the latter.

The $MS^2$ spectrum illustrated in FIG. 3(a) shows the result of an $MS^2$ analysis in which an ion having a mass-to-charge ratio of m/z500 is selected as a precursor ion. On the other hand, the $MS^2$ spectrum illustrated in FIG. 3(b) shows the result of an $MS^2$ analysis in which, with respect to the same sample, an ion having a mass-to-charge ratio of m/z800 is selected as a precursor ion. If a person in charge of the analysis compares the peaks appearing on these $MS^2$ spectra, it is quite obvious that common virtual peaks of the mass-to-charge ratio of 100 and 320 exist. Therefore, it is immediately known that there are two ions, although their precursor ion's mass-to-charge ratio is different, having a fragment, which is desorbed by a dissociation, with a common mass.

In the example of FIG. 3, an $MS^n$ spectrum and $MS^n$ mass-to-charge ratio difference spectrum as described in the present invention are completely overlapped and the display color of the peaks included in each spectrum is changed so that they are discriminable. However, instead of the display color, the line type and line thickness may be changed.

Figure 4:
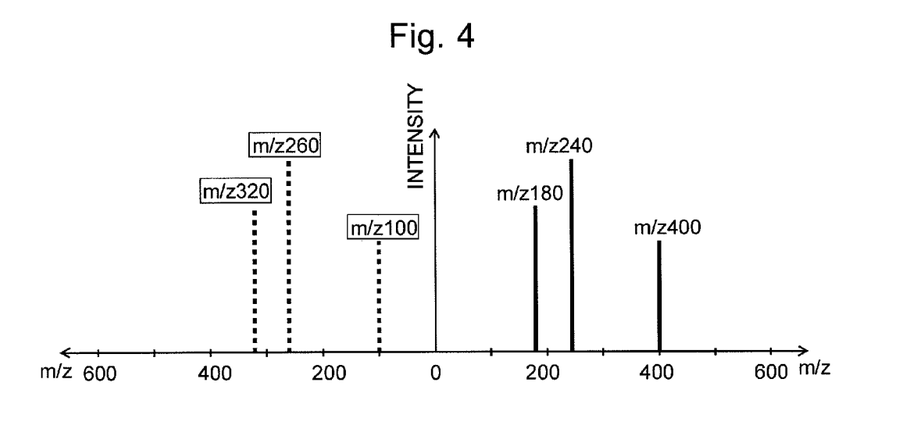
FIG. 4 is a diagram illustrating another example of the display of an MS$^n$ spectrum in the mass analytical system according to the present embodiment.
Figure 5:
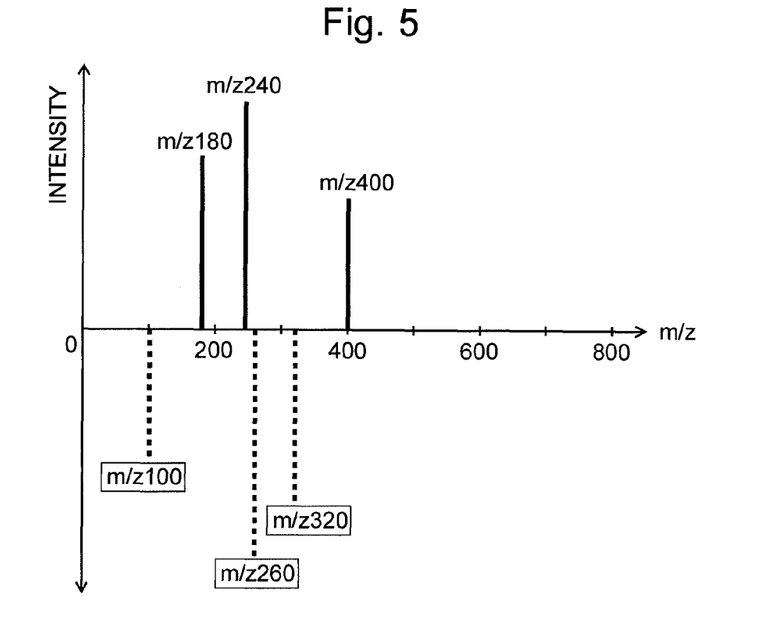
FIG. 5 is a diagram illustrating another example of the display of an MS$^n$ spectrum in the mass analytical system according to the present embodiment.
Figure 6:
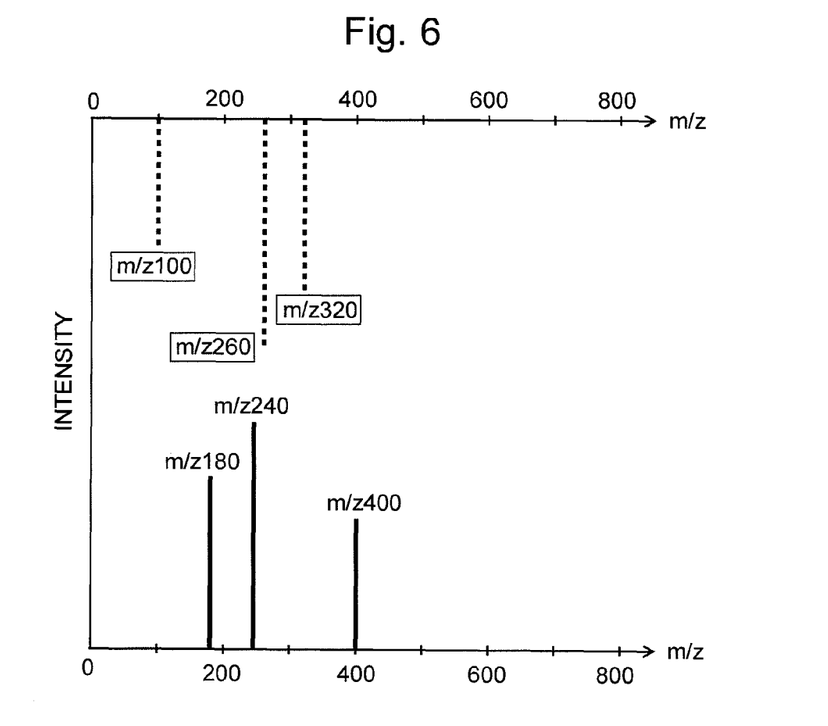
FIG. 6 is a diagram illustrating another example of the display of an MS$^n$ spectrum in the mass analytical system according to the present embodiment.

Other embodiments as illustrated in FIGS. 4 through 6 may be possible. In FIG. 4, the mass-to-charge ratio axes are not overlapped but they are line-symmetrically extended centering on the intensity axis (i.e. they are left-right symmetrical). In FIG. 5, the mass-to-charge ratio axes are overlapped, whereas the intensity axes are not overlapped but they are line-symmetrically extended centering on the mass-to-charge ratio axis (i.e. they are vertically symmetrical). In FIG. 6, the mass-to-charge ratio axis of the $MS^n$ mass-to-charge ratio difference spectrum of FIG. 5 is moved in parallel. In these embodiments, since the peak existence regions of both spectra do not overlap, these two spectra can be well distinguished without changing the peak's line type. Alternatively, the type of the mass label may be changed (e.g. displaying the text of one spectrum in italic face or changing the shape of the display box, etc) so that the peaks in both spectra can be distinguished.

In each example of FIGS. 3 through 6, the relative intensity of a virtual peak is set to be the same as that of the peak of the original product ion. However, the relative intensity of a virtual peak can be appropriately changed. For example, it may be set to be a given relative intensity regardless of the relative intensity of the original product ion. Alternatively, in the case where the relative intensity is so low that the peak is hardly visible, the relative intensity may be appropriately increased to improve the visibility.

In the aforementioned embodiment, the created mass-to-charge ratio difference spectrum has a peak at a position of the mass-to-charge ratio difference between the precursor ion and a product ion of an $MS^n$ analysis. However, in the case where n is equal to or more than three and the dissociation operation is performed in multiple stages, a mass-to-charge ratio difference spectrum may be created which has a peak at a position of the mass-to-charge ratio difference between the product ion of the $MS^n$ analysis and the precursor ion of the $MS^{n-1}$ analysis which has been the basis of the creation of the precursor ion, or, further going back, the precursor ion of the $MS^{n-2}$ analysis. That is, a spectrum may be created based on the mass-to-charge ratio difference between the product ion obtained by an $MS^n$ analysis and the precursor ions of $MS^n$ through $MS^{n-1}$ analyses. Such a mass-to-charge ratio difference spectrum is particularly useful in the following case.

As an example, suppose that a substance A (with a mass-to-charge ratio of m/z1000) was observed in an $MS^n$ analysis; then, using this as the precursor ion, an $MS^2$ analysis was performed, with the result that the product ion with a mass-to-charge ratio of m/z982 was observed; and finally, using this product ion as the precursor ion, an $MS^3$ analysis was performed, with the result that three kinds of product ions of m/z300, 500, and 800 were observed. In this case, the mass-to-charge ratio differences between the product ions of the $MS^3$ analysis and the precursor ion are 682, 482, and 182. In the meantime, suppose that a substance A' (with a mass-to-charge ratio of m/z1100) which is similar to the substance A was observed in an $MS^1$ analysis, and using this substance A' as the precursor ion because it is easy to be dissociated, an $MS^2$ analysis was performed, with the result that four kinds of product ions of m/z1082, 900, 600, and 400 were observed. It is possible to deduce that each product ion originating from the substance A' consists of a product ion observed in the $MS^2$ or $MS^3$ analysis of the substance A and an additional element with the mass of 100.

Therefore, for example, it is possible to assume that the product ion with a mass-to-charge ratio of m/z400 originating from the substance A' is highly similar to the product ion with a mass-to-charge ratio of m/z300 originating form the substance A. However, the mass-to-charge ratio difference between the product ion and precursor ion of the $MS^2$ analysis obtained from the former product ion is 700, and the mass-to-charge ratio difference between the product ion and precursor ion of the $MS^3$ analysis obtained from the latter product ion is 682. Since these two mass-to-charge ratio differences are different, it is not possible to find the similarity between the product ions only by simply checking the mass-to-charge ratio difference between the ions before and after the dissociation operation as previously described.

Given this factor, in order to prevent a sort of overlooking of the commonality and similarity as described earlier, it is preferable that not only the mass-to-charge ratio difference between the precursor ion and the product ion obtained by one dissociation operation of that precursor ion may be calculated to create a spectrum but also the mass-to-charge ratio difference between the product ion and the precursor ion of the dissociation operation in the previous stage which has produced the aforementioned precursor ion or the precursor ion of the dissociation operation in further previous stage may be calculated to create a spectrum to be displayed. In the aforementioned example, for the product ion with a mass-to-charge ratio of m/z300 originating from the substance A, not only is the mass-to-charge ratio difference with the precursor ion (with a mass-to-charge ratio of m/z982) in the $MS^3$ analysis calculated, but the mass-to-charge ratio difference with the precursor ion (with a mass-to-charge ratio difference of m/z1000) in the $MS^2$ analysis, which is the previous stage of the $MS^3$ analysis, also may be preferably calculated, and the calculated results may be displayed on the $MS^n$ mass-to-charge ratio difference spectrum. Therefore, the similarity and commonality of the product ions originating from precursor ions having different mass-to-charge ratios can be assuredly obtained better than before.

In both cases where an $MS^n$ spectrum and a mass-to-charge ratio difference spectrum are overlapped to be displayed and where they are displayed in other areas, it is preferable that, for a given peak on the mass-to-charge ratio difference spectrum, which peak in the $MS^n$ spectrum is used for the subtraction with the precursor ion can be understood at a glance. Given this factor, in the case where no peak of the precursor ion appears for example, this may be virtually illustrated so that it is discriminable with other peaks. Then, this peak, the product ion's peak, and a peak on the mass-to-charge ratio difference spectrum depending on these peaks may be associated in the manner such as: conforming their display color, uniting them with a line, or indicating them with the same sign. A display for illustrating such a correspondence relationship do not need to be permanently performed. For example, if a person in charge of the analysis selects a desired peak on a mass-to-charge ratio difference spectrum by operating a mouse of the operation unit 13 or by other operation, the display color of the peaks of the product ion and precursor ion corresponding to the selected peak may be changed, their brightness may be changed, etc., so that they can be easily and temporarily recognizable.

Figure 7:
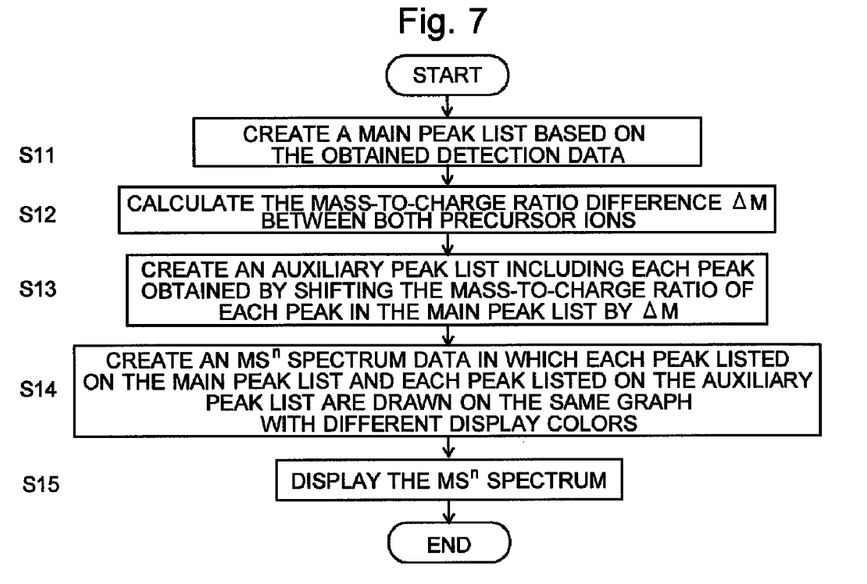
FIG. 7 is a flowchart illustrating the operation of an MS$^n$ spectrum display processing in the mass analytical system according to another embodiment of the present invention.

Next, an embodiment of a mass analytical system having a data processor according to the second aspect of the present invention will be explained. The explanation for the overall configuration of this mass analytical system is omitted because it is the same as illustrated in FIG. 1 which is the embodiment of the first aspect of the present invention as described earlier. What is different is only a processing operation in creating, in the data processor 12, an MS$^n$ spectrum to be displayed on the display unit 14. FIG. 7 illustrates a flowchart of this processing operation, and FIG. 8 illustrates an example of an MS$^2$ spectrum displayed as a result of an MS$^2$ analysis.

Figure 8:
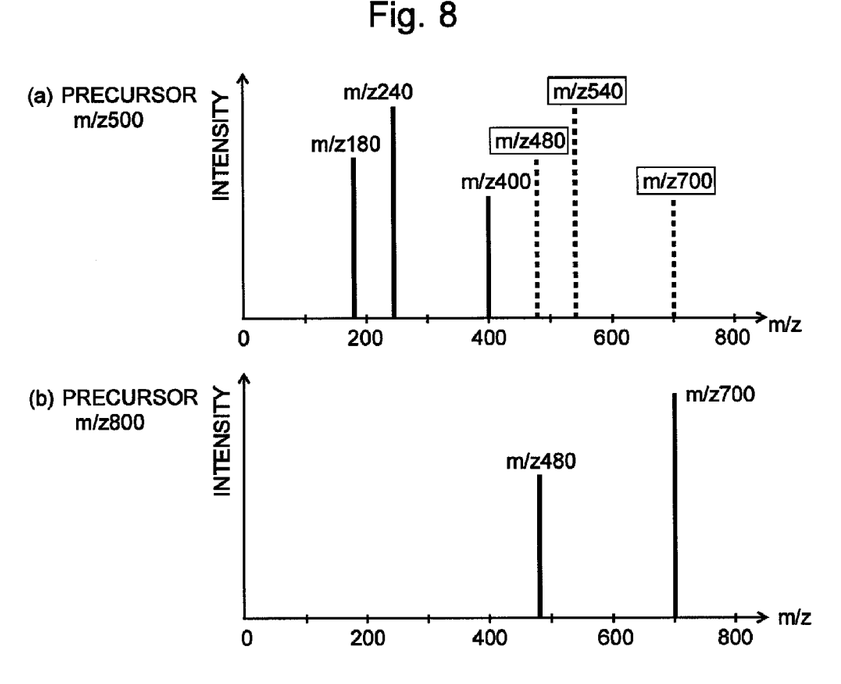
FIG. 8 is a diagram illustrating an example of the display of an MS$^n$ spectrum in the mass analytical system according to another embodiment of the present invention.

In this case, the display of the MS$^2$ spectrum in which an ion with a mass-to-charge ratio of m/z800 has been set to be the precursor ion does not make any difference with conventional FIG. 9(*b*) as illustrated in FIG. 8(*b*). On the other hand, the display of the MS$^2$ spectrum in which an ion with a mass-to-charge ratio of m/z500 has been set to be the precursor ion includes, as illustrated in FIG. 8(*a*), virtual peaks in addition to the real peaks originating from the product ions.

That is, receiving the detection data of the MS$^2$ analysis in which an ion with a mass-to-charge ratio of m/z500 has been set to be the precursor ion, the data processor 12 creates a main peak list in which the mass-to-charge ratio and the relative intensity according to the ion current's magnitude are associated (Step S11). Next, the data processor 12 calculates the difference ΔM between the mass-to-charge ratio of this precursor ion (m/z500) and that of the precursor ion of the MS$^2$ analysis to be compared (m/z800) in Step S12, and creates an auxiliary peak list including each peak obtained by shifting the mass-to-charge ratio of each product ion appearing on the MS$^n$ spectrum (i.e. listed on the main peak list) by the mss-to-charge ratio difference ΔM (Step S13). In the example of FIG. 8(*a*) for instance, since the precursor ion's mass-to-charge ratio difference ΔM is 300, the peaks corresponding to each product ion having the mass-to-charge ratio of M1, M2, and M3 of 180, 240, and 400 respectively are shifted on the mass-to-charge ratio axis by 300. Since the mass-to-charge ratio of the precursor ion to be compared is larger in this case, they are shifted upward. Consequently, an auxiliary peak list for forming peaks at each position of m/z480, 540, and 700 is created.

In the next step and on the same graph, i.e. on the graph having a common mass-to-charge ratio axis and intensity axis, each peak listed on the main peak list is drawn with a line having a predetermined display color (e.g. black), and each peak listed on the auxiliary peak list is drawn with a line having another display color (e.g. red), so that an MS$^n$ spectrum data is created (Step S14). Then the MS$^n$ spectrum data is sent to the central controller 10 to be displayed on the screen of the display unit 14, and consequently the MS$^n$ spectrum as illustrated in FIG. 8(*a*) is drawn (Step S15).

When a person in charge of the analysis compares the peaks appearing on the MS$^2$ spectra as illustrated in FIGS. 8(*a*) and (*b*), the person instantly understands that common peaks are existent at the mass-to-charge ratios m/z of 480 and 700 in the MS$^2$ analysis in which the precursor ion's mass-to-charge ratio m/z is 800. Since the operation of peak's mass-to-charge ratio shift as described earlier corresponds to the operation of correcting the both precursor ions' mass-to-charge ratio difference, based on the aforementioned result, it is immediately known that there are two ions, although their precursor ion's mass-to-charge ratio is different, having a fragment, which is desorbed by a dissociation, with a common mass.

In the aforementioned example, the peaks appearing on the MS$^2$ spectrum in which the precursor ion's mass-to-charge ratio m/z is 500 have been shifted. However, the peaks appearing on the MS$^2$ spectrum in which the precursor ion's mass-to-charge ratio m/z is 800 may be shifted (downward in this case) to obtain the same result.

Also in this embodiment as in the previously described embodiment, in order to discriminate between a peak originating from an original product ion and a virtual peak obtained by a shift, a variety of illustrations can be used other than changing the display color.

It should be noted that, also in other aspects, it is evident that any modification, adjustment or addition properly made within the spirit of the preset invention is also covered within the scope of the claims of this patent application.

The invention claimed is:

1. A data processor for a mass spectrometer, for processing data obtained by a mass spectrometer capable of performing an MS$^n$ analysis in which an ion having a specific mass-to-charge ratio is selected as a precursor ion from among ions obtained by an MS$^{n-1}$ (where n is an integer equal to or more than two) analysis and an MS$^n$ analysis of an ion generated by a dissociation operation for the precursor ion is performed, comprising:
   a) an MS$^n$ spectrum creator for creating spectrum data for displaying an MS$^n$ spectrum based on data obtained by an MS$^n$ analysis;
   b) a mass-to-charge ratio difference calculator for calculating each difference between a mass-to-charge ratio of all or a portion of peaks appearing on the MS$^n$ spectrum and a mass-to-charge ratio of a precursor ion of the MS$^n$ analysis and/or a precursor ion of an MS$^2$ analysis through MS$^{n-1}$ analysis (where n is equal to or more than three in this case) which have been a basis of a creation of the MS$^n$ analysis' precursor ion;
   c) an MS$^n$ mass-to-charge ratio difference spectrum creator for creating mass-to-charge ratio difference spectrum data for displaying an MS$^n$ mass-to-charge ratio difference spectrum having a peak at a position of each mass-to-charge ratio difference obtained by the mass-to-charge ratio difference calculator; and
   d) a spectrum merge section for creating a spectrum in which the MS$^n$ mass-to-charge ratio difference spectrum and the MS$^n$ spectrum are overlapped or combined so that each peak appearing on both spectra can be visually discriminable, and
   the data processor for a mass spectrometer displaying the spectrum created by the spectrum merge section on a display screen.

2. The data processor for a mass spectrometer according to claim 1, wherein each peak appearing on both spectra can be visually discriminable in that a color, thickness and/or type of a line of a peak appearing on the MS$^n$ spectrum and the MS$^n$ mass-to-charge ratio difference spectrum is different.

3. The data processor for a mass spectrometer according to claim 1, wherein mass-to-charge ratio axes of the spectra are line-symmetrically extended centering on an intensity axis, so that each peak appearing on both spectra can be visually discriminable.

4. The data processor for a mass spectrometer according to claim 1, wherein intensity axes of the spectra are line-symmetrically extended centering on the mass-to-charge ratio axis, so that each peak appearing on both spectra can be visually discriminable.

5. A data processor for a mass spectrometer, for processing data obtained by a mass spectrometer capable of performing an MS$^n$ analysis in which an ion having a specific mass-to-charge ratio is selected as a precursor ion from among ions obtained by an MS$^{n-1}$ (where n is an integer equal to or more than two) analysis and an MS$^n$ analysis of an ion generated by a dissociation operation for the precursor ion is performed, comprising:
   a) an MS$^n$ spectrum creator for creating spectrum data for displaying an MS$^n$ spectrum based on data obtained by an MS$^n$ analysis; and b) an MS″ spectrum modifier for, in a case where two precursor ions whose mass-to-charge ratio is different from each other are set to respectively perform an MS″ analysis, calculating a mass-to-charge ratio difference between the two precursor ions and adding spectrum data so that a virtual peak in which a position of all or a portion of peaks appearing on the MS″ spectrum is shifted by the mass-to-charge ratio difference is displayed on the MS″ spectrum, and the data processor for a mass spectrometer displaying a spectrum based on the spectrum data added by the MS″ spectrum modifier on a display screen.

6. The data processor for a mass spectrometer according to claim 5, wherein the virtual peak is displayed to be visually discriminable.

\* \* \* \* \*